(12) United States Patent
Kirchner et al.

(10) Patent No.: US 12,383,280 B2
(45) Date of Patent: Aug. 12, 2025

(54) LIGATURE DEVICE FOR BODY PARTS

(71) Applicant: KIMETEC GMBH, Ditzingen (DE)

(72) Inventors: Claudia Kirchner, Markgröningen (DE); Hansjörg Kirchner, Markgröningen (DE); Caroline Ihle, Markgröningen (DE)

(73) Assignee: KIMETEC GMBH, Ditzingen (DE)

( * ) Notice: Subject to any disclaimer, the term of this patent is extended or adjusted under 35 U.S.C. 154(b) by 398 days.

(21) Appl. No.: 18/024,237

(22) PCT Filed: Jun. 21, 2021

(86) PCT No.: PCT/EP2021/066864
§ 371 (c)(1),
(2) Date: Mar. 1, 2023

(87) PCT Pub. No.: WO2022/053193
PCT Pub. Date: Mar. 17, 2022

(65) Prior Publication Data
US 2023/0320736 A1      Oct. 12, 2023

(30) Foreign Application Priority Data
Sep. 9, 2020 (DE) ...................... 10 2020 123 496.1

(51) Int. Cl.
*A61B 17/132* (2006.01)
*A61B 17/00* (2006.01)

(52) U.S. Cl.
CPC ............ *A61B 17/1327* (2013.01); *A61B 2017/00862* (2013.01); *A61B 2017/00955* (2013.01)

(58) Field of Classification Search
CPC .............. A61B 17/1327; A61B 17/132; A61B 17/1322; A61B 2017/00862; A61B 2017/00955
See application file for complete search history.

(56) References Cited

U.S. PATENT DOCUMENTS

| 4,640,281 A | * | 2/1987 | Sturm | ............... A44B 11/25 24/115 M |
| 5,084,062 A | * | 1/1992 | Sturm | ............... A44B 11/25 24/168 |

(Continued)

FOREIGN PATENT DOCUMENTS

| EP | 1458296 | 6/2006 |
| WO | WO 2019057784 A2 | 3/2019 |

*Primary Examiner* — Ryan J. Severson
(74) *Attorney, Agent, or Firm* — John Alumit (57) ABSTRACT

The invention relates to a ligature device for body parts, in particular a tourniquet, comprising a closure housing (2) in which a feed-through shaft (230) is formed which extends in the longitudinal direction and is delimited at the bottom by a base wall (27), laterally by two lateral walls (26, 26') and at the top by a top wall (24), and comprising a ligature strap (3) which, by means of a clipping buckle (5) fastened to the one rear end thereof, is clipped or can be clipped detachably to a rear portion of the closure housing (2) and, with the other end thereof, is guided or can be guided from the rear side through the feed-through shaft (230) in order to form a loop (31) of variable size and can be firmly clamped according to the size of a received body part by means of a clamping means, in particular by means of a rocker (4) that is pivotally mounted in a pivot bearing in the closure housing (2). Advantageous performance characteristics result from the fact that the ligature strap (3) is produced from a rubber-elastic material, such as natural rubber, a thermoplastic elastomer (TPE) or from silicone.

12 Claims, 4 Drawing Sheets

(56) References Cited

U.S. PATENT DOCUMENTS

| | | | | |
|---|---|---|---|---|
| 5,314,437 A * | 5/1994 | Holtsch | ............. | A61B 17/1327 606/151 |
| 5,535,485 A * | 7/1996 | Kirchner | ............ | A61B 17/1327 606/203 |
| 5,653,728 A * | 8/1997 | Ahern | ................ | A61B 17/1322 606/203 |
| 6,217,601 B1 * | 4/2001 | Chao | .................. | A61B 17/1327 606/203 |
| 6,250,047 B1 * | 6/2001 | Ahern | ................ | A61B 17/1322 53/430 |
| 7,320,699 B2 * | 1/2008 | Kirchner | ............ | A61B 17/1327 606/203 |
| 2004/0127938 A1 * | 7/2004 | Kirchner | ............ | A61B 17/1327 606/203 |
| 2008/0312682 A1 * | 12/2008 | Shams | ............... | A61B 17/1327 606/203 |
| 2011/0247179 A1 * | 10/2011 | Bellamy | ........... | A61B 17/1327 24/19 |
| 2012/0296369 A1 * | 11/2012 | Atthoff | ............. | A61B 17/1322 606/202 |
| 2017/0273694 A1 * | 9/2017 | Lynch | .................... | A61B 90/08 |
| 2020/0297352 A1 * | 9/2020 | Altrichter | ............ | A61B 17/135 |
| 2021/0236141 A1 * | 8/2021 | Brikman | ............ | A61B 17/135 |
| 2023/0320736 A1 * | 10/2023 | Kirchner | ............ | A61B 17/1327 606/203 |

\* cited by examiner

LIGATURE DEVICE FOR BODY PARTS

The invention relates to a ligature device for body parts, in particular a tourniquet, comprising a closure housing in which a feed-through shaft is formed which extends in the longitudinal direction and is delimited at the bottom by a base wall, laterally by two lateral walls and at the top by a top wall, and comprising a ligature strap which, by means of a clipping buckle fastened to the one rear end thereof, is clipped or can be clipped detachably to a rear portion of the closure housing and, with the other end thereof, is guided or can be guided from the rear side through the feed-through shaft in order to form a loop of variable size and can be firmly clamped according to the size of a received body part by means of a clamping means, in particular by means of a rocker that is pivotally mounted in a pivot bearing in the closure housing.

A ligature device of this type is specified in EP 1 458 296 B1. In the case of this known ligature device for body parts, a feed-through shaft for a ligature strap is formed in a closure housing having a base wall, two lateral walls and a top wall on its top side, the feed-through shaft being open on the rear side and the front side of the closure housing. The ligature strap is provided with a clipping buckle at its rear end and can be detachably clipped via the latter in a rear portion of the closure housing and can be guided with its front end from the rear of the closure housing through the feed-through shaft to form a loop of variable size, so that a body part to be ligated can be received in the loop and can be ligated with a required tension, e.g., to prevent venous blood flow. The ligature strap is clamped under the tension condition set by an operator in the closure housing by means of a rocker against an intermediate wall formed in the closure housing and can be released to release the tension condition by operating the rocker to increase the size of the loop. By unclipping the clipping buckle, it can be pulled out of the closure housing and the loop can be fully opened. Both from the point of view of the person to be treated and the user who has to concentrate on the actual treatment measures, the best possible functionality of the ligature device, which also includes high hygienic requirements, is of great importance.

A ligature device similar to the basic structure, such as the one mentioned above, is also shown in EP 0 633 747 B1.

A ligature device that is particularly suitable for single use, is more cost-effective and easier to produce, in particular in the form of a tourniquet, is presented in EP 3 068 314 B1. In this case, the ligature strap is provided with a simple locking device, in particular a hook-and-loop fastener, and for this purpose consists of a fluffy material which forms loops for the hook-and-loop locking and comprises, for example, a loop fabric or a spunbonded fabric, i.e., is composed of threads or tiny hair, wherein viscose, polyester or polypropylene are referred to as suitable materials. The material is flexible and can have an inherent elasticity.

DE 44 12 832 A1 shows an autoclavable cuff which can be designed as a Tourniquet cuff or as a blood pressure cuff. In this case, a core formed as an elongated tube is glued onto a flat base, wherein the base and the core consist of a material which can be sterilized by steam sterilization, for example made of silicone. In particular, the base consists of harder silicone material than the core. Such a multi-layered structure of the ligature strap is fraught with disadvantages for a tourniquet with a closure housing that is as compact as possible and easy to operate with one hand.

In a ligature device for body parts, in particular tourniquet, disclosed in EP 0 566 036 A2, a ligature strap is guided through a closure housing and is clamped therein in its tensioned state applied to a body part by means of a rocker pivotally mounted about an axis against a housing wall. The rocker is not only pivotally mounted on the axle held firmly in the housing, it is also guided for limited displacement in the longitudinal direction. A spring which is supported on the axle acts on a cranked leg of the rocker and tries to push it into the open position. When the ligature device is applied, the rocker is pulled against the force of the spring into its position opposite to the open position as a result of the ligature tension in the ligature strap. To release and open the ligature strap, the rocker is pivoted from its clamping position to a release position by means of a manual release pressure on a pushbutton, which also forms part of a locking closure. After temporarily interrupting the manual release pressure on the pushbutton, the spring can displace the rocker further into the open position, after which the locking closure and thus the loop formed by the ligature strap can be opened. The closure housing has design features that are delicately matched to this particular functional mechanism, wherein both the release of the ligature and the opening of the loop are performed by manually operating the push button. In this case, the spring is used to displace the rocker; the pivoting of which takes place via the ligature strap for clamping and via the pushbutton for releasing and opening. No further details are given about the construction of the ligature strap.

The object of the present invention is to provide a ligature device for body parts, in particular in the form of a tourniquet, of the type mentioned above, which has optimized functional properties both from the point of view of the person to be treated and of the user.

This object is achieved in a ligature device having the features of claim 1. Here, in a ligature device, in particular a tourniquet, having the features mentioned in the preamble, it is provided that the ligature strap is made of elastic material, such as a natural rubber, thermoplastic elastomer (TPE) or, in particular, of silicone, i.e., as a silicone strap. As the inventors have found, the ligature strap thus formed in a rubber-elastic manner, in particular a one-piece silicone strap preferably formed as a solid profile, has substantial advantages both for handling in cooperation with the closure housing and also for the functionality of the ligature device due to its conformability around the skin of the body part to be ligated and a certain elasticity for dosing the ligature tension and, moreover, due to its hygienic properties. On the one hand, due to its good sliding properties (low friction) in the unstressed state, the ligature strap can be easily guided in the closure housing and in the hand, and, on the other hand, due to its rubber-elastic texture, it can be firmly clamped in the feed-through shaft of the closure housing by means of the rocker and/or housing structure engaging in the strap material. The one-piece design, in particular as a solid profile, has advantages for the construction, function and handling.

If it is provided that the ligature strap has a smoothed and/or hardened surface, improved sliding properties are achieved both on the skin of the person to be treated and during displacement in the closure housing, since friction (in particular static friction, but also sliding friction) is reduced. The smoothing of the surface and/or hardening of the ligature strap, in particular a silicone strap or TPE strap, can thereby be favorably influenced by the introduction of additives which determine these properties or, for example, also by treatment with UV radiation. Here, it is also possible to match the material and structures of the closure housing, and optimization can be achieved by practical experiments or simulation.

An advantageous measure for achieving a smoothed and hardened surface is, for example, that the surface is smoothed and hardened by fluoride treatment of a rubber-elastic strap, in particular a silicone strap, from which the ligature strap is made.

Furthermore, the measures that are advantageous for production and function are that the ligature strap (in particular one-piece, preferably designed as a solid profile) has a rectangular cross-section, wherein the width of the ligature strap is between 10 and 40 mm, preferably between 20 and 30 mm, and the thickness of the ligature strap is between 0.8 and 3 mm, preferably between 1 and 2.5 mm.

Good grip combined with good sliding properties (low frictional influences) is further facilitated by the fact that the top side of the strap and/or the bottom side of the strap is provided with a friction-reducing or low-friction relief-like structure. The good sliding properties are obtained or retained while reducing the contact surfaces or friction surfaces between the ligature strap and facing surface regions in the closure housing. The grip and the sliding capability or respectively low friction (which is more related to the microstructure of the contacting surface regions) can be optimized empirically through experiments.

In order to enable the operator to easily check the state of tension exerted via the loop of the ligature strap on the part of the body to be ligated, it is advantageously provided that the ligature strap is provided with a marking which changes as it is stretched, by means of which a state of tension of the ligature strap corresponding to a ligature tension can be identified.

To meet hygienic requirements, it can advantageously be provided that the ligature strap is transparent, in particular also for radiation in the UV range, wherein in particular a transparency in the UVC range is particularly advantageous for hygienic reasons.

Accordingly, the measures that the closure housing is transparent to UV radiation, in particular UVC radiation, also contribute to the advantageous hygienic treatment of the ligature device, since harmful germs such as viruses, bacteria, fungi and other pollutants are reached and rendered harmless by the UV radiation even in places in the closure housing that are difficult to access with cleaning fluid or mechanical cleaning agents.

In addition, the UV radiation can be used to cause intentional aging, in particular as a result of a discernible change in the transparency or a color effect, in order to discard ligature devices that are already older.

In order to achieve favorable sliding properties of the ligature strap in the feed-through shaft of the closure housing, it is furthermore advantageously provided that, in the feed-through shaft on at least one side facing the top side of the strap and/or the bottom side of the strap, rib-like sliding structures extending in the longitudinal direction of the closure housing protruding from wall portions or from an optionally present rocker are arranged. This avoids large, unfavorable friction surfaces between the ligature strap and facing effective surfaces in the closure housing.

Furthermore, for function and handling, the measures are advantageous that the rocker is supported on its bottom side in its rear portion located towards the rear side behind the pivot bearing against the top side of the base wall by means of a spring arrangement by means of which the rocker is brought into its non-clamping rest position when the loop is unstressed. This allows the ligature strap to be easily displaced in the closure housing when released from the tension state in order, for example, to pre-adjust a suitable loop size or to move the closure housing to a desired position relative to the ligature strap, e.g., for donning, doffing or storing.

One advantageous design is that the spring arrangement is formed as a return spring which is integrally formed on the rocker and projects towards the base wall.

Advantages for handling, such as storage, are further provided by the fact that the ligature strap is provided at its other end, the front end, facing away from the clipping buckle with an end piece designed as a fastener.

The invention is explained in more detail below by means of exemplary embodiments with reference to the drawings. In the drawings.

Figure 1:
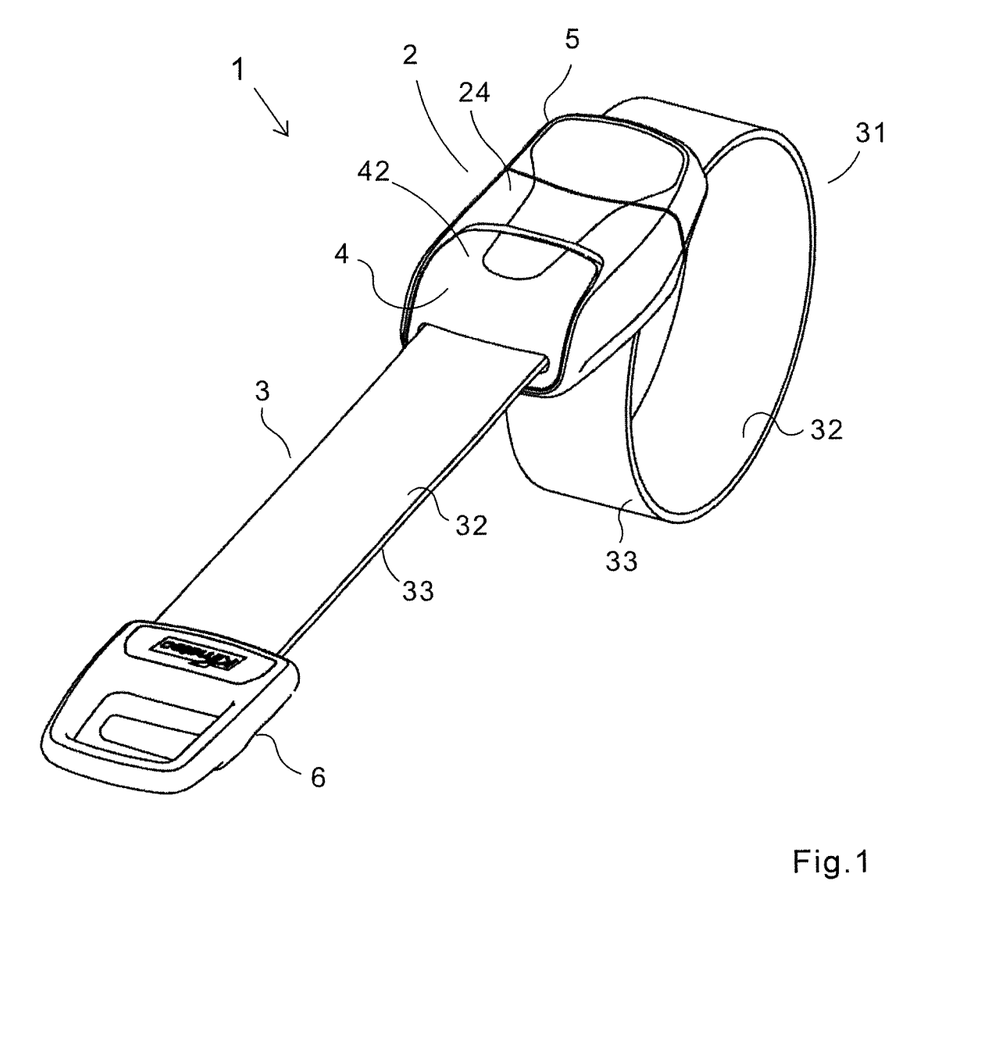
FIG. 1 shows a perspective view of a ligature device with a ligature strap guided through a closure housing and forming a loop.

FIG. 1 is a perspective view of an embodiment of a ligature device 1 with its essential components, namely a closure housing 2, a rocker 4 pivotably mounted therein, and a ligature strap 3 which is guided in the longitudinal direction through a feed-through shaft, which is open on its rear side and its front side, in the interior of the closure housing 2 and is detachably clipped to a clipping buckle 5 in a rear end portion of the closure housing 2 while forming a loop 31 of variable size. The ligature strap 3 is fastened by its rear (back) end or end portion to the clipping buckle and, while forming the loop 31, is guided from the direction of the rear side of the closure housing 2 through the feed-through shaft, which is open on its rear side, above a rocker plate of a rocker 4 (not visible in FIG. 1) in the longitudinal direction through the closure housing 2 and out of the closure housing 2 through a feed-through opening 43 formed in the front side of the rocker 4. At its other, front end or end portion, the ligature strap 3 is provided with an end piece 6 serving as a fastener. According to FIG. 1, the closure housing 2 has a top wall 24 on its top side, laterally on each side a lateral wall (only one of which is visible in FIG. 1) and a base wall (only slightly visible in FIG. 1) surrounding the feed-through shaft at the top, laterally and at the bottom.

By means of the rocker 4 pivotably mounted in a pivot bearing in the closure housing 2, the ligature strap 3 can be clamped downwards (with a force component) by pulling on the portion of the loop 31 adjacent to the rear side of the closure housing 2 as shown in FIG. 1. Pulling the portion of the ligature strap 3 passing from the loop 31 into the feed-through shaft causes the portion of the rocker 4 located behind the pivot bearing to be pivoted downward and the portion of the rocker 4 located in front of the pivot bearing to be pivoted upward, and the ligature strap 3 running over the rocker 4 is pressed by the front part of the rocker plate against an abutment (not visible in FIG. 1) that is fixedly attached in the closure housing 2 above the ligature strap 3, and is thereby clamped. As a result, a loop width required for ligature of a body part received in the loop can be fixedly adjusted, since by means of a pull on the portion of the ligature strap 3 guided out on the front side of the closure housing 2 the body part to be ligated itself pulls downwards the portion of the ligature strap 3 entering at the rear side of the closure housing 2 via the rocker 4.

The front portion of the rocker 4 is provided with an actuating portion 42 integrally formed on the rocker plate 41, which projects upwards and rearwards from the transition region located in the front between the rocker plate and the actuating portion 42 under convex curvature into a recess of a corresponding contour formed into the front region of the top wall 24 of the closure housing 2. By pressing the actuating portion 42, the ligature strap 3, which is pressed with its top side 32 against the abutment of the closure housing 2 by means of the front portion of the rocker plate located in front of the pivot bearing and thus clamped, can be released or clamped in a metered manner. As a result, the loop 31 can be varied in its width (diameter or circumference) and thus the ligature strap 3 can be fixed under the desired ligature tension in a corresponding tension state on the body part to be ligated. By unclipping the clipping buckle 5, the loop 31 can be fully opened and thus the ligature device 1 can be removed from the body part to be ligated and, conversely, by clipping the clipping buckle 5 in the closure housing 2 with a correspondingly preselected loop size, it can be applied around a body part to be ligated. Here, the top side of the strap 33 of the ligature strap 3 forms the inner side of the loop 31 facing the body part. This structure and this function are also shown in EP 1 458 296 B1 mentioned above.

Figure 2A:
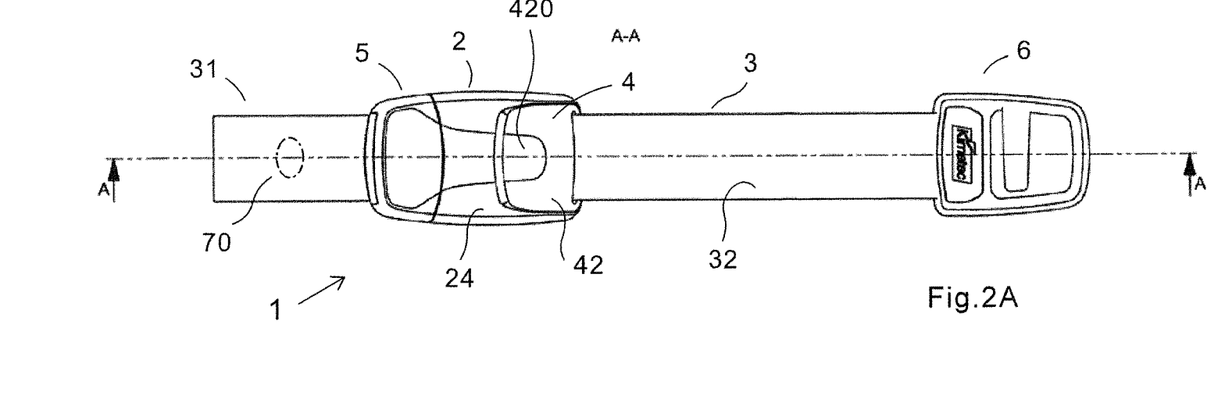
FIG. 2A shows a plan view of the ligature device according to FIG. 1.
Figures 2B, 2C:
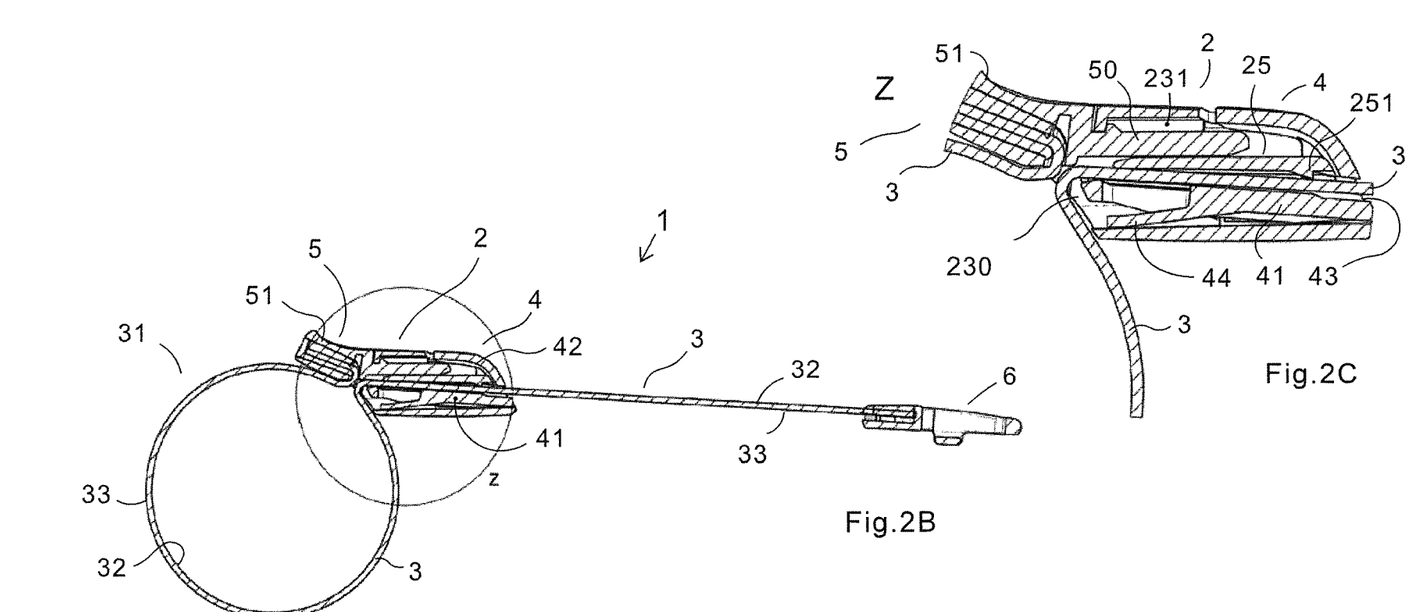
FIG. 2B shows a sectional side view of the ligature device along a section line A-A according to FIG. 2A.
FIG. 2C shows an enlarged section Z of the ligature device according to FIG. 2B in the region of the closure housing.

In further FIGS. 2A, 2B, 2C; 3A, 3B; 4A, 4B, 4C, 4D, 4E and 4F, the essential components of the ligature device 1 and also the differences from the ligature device 1 presented in EP 1 458 296 B1 are shown in more detail.

In contrast to the embodiment shown in EP 1 458 296 B1 and also in EP 0 633 747 B1, in the ligature device according to the present invention shown in FIG. 1 and FIGS. 2A, 2B and 2C, the ligature strap 3 (in particular one-piece and preferably as a solid profile) is made of an elastic material, such as natural rubber, a thermoplastic elastomer (TPE) or, particularly preferably, of silicone as a (one-piece) silicone strap. The ligature strap, in particular silicone strap, formed in this way has, given the usual bandwidth of the ligature device 1 of between, for example, 10 and 40 mm, preferably between 20 and 30 mm, and a strap thickness of between, for example, 0.8 and 3 mm, preferably between 1 and 2.5 mm, as is expedient in particular in the form of a tourniquet, an inherent flexibility and also elasticity, in particular rubber elasticity, which is advantageous for the function. As a result, the ligature strap 3 can advantageously adapt its shape well to different circumferential contours and tissue properties of the skin and skin surface and, primarily as a silicone strap, also exhibits good conformability or respectively good haptic properties.

In order to improve sliding on the skin and also between facing wall regions within the closure housing 2 and the rocker 4, the ligature strap 3 produced as a silicone strap or from the rubber-elastic material is smoothed and/or hardened (with respect to its inner region) as a whole or only on its top side 32 and/or bottom side 33 by chemical, mechanical or physical treatment, for example by adding additives influencing the sliding properties and/or the hardness during production or by treatment by means of UV radiation. For example, this treatment consists of fluoride treatment. The top side of the strap 32 and/or the bottom side of the strap 33 may additionally be provided with relief-like, molded-in structures that improve the grip, which provide haptic advantages both for the handling by the user and for the feel by the person to be treated and also result in advantages for the sliding of the ligature strap 3 in the closure housing 2 and its clamping in the closure housing 2. The improved sliding (in the unstressed or slightly stressed state of the ligature strap) can thereby be influenced by the reduced contact surface or friction surface and by the surface structure between the ligature strap and facing surface regions in the interior of the closure housing. Here, the top side of the strap 32 and the bottom side of the strap 33 are designed in a smooth or relief-structured finish with regard to good, easy cleanability, in order to meet high hygienic requirements.

Advantageously, the ligature strap 3 may be provided with a marking 70 to allow the user to easily check the tension state of the loop 31 applied to a body part to be ligated. For example, the marking 70 consists of a geometric pattern embossed or printed on the top side of the strap 32 facing the user, such as, for example, an ellipse with a large diameter extending transversely (at right angles) to the longitudinal direction of the ligature strap 3, which deforms into an easily recognizable circle when the required ligature tension is applied and the loop 31 is under a given state of tension as a result of the elasticity of the ligature strap 3. Other geometric patterns with an easily recognizable, defined marking change (such as, for example, a rectangle changing to a square) are also suitable. For example, such a tension state attained in a tourniquet corresponds to a ligature tension that withstands a pressure of between 5 mm Hg and 40 mm Hg, for example 10 mm Hg or less than 25 mm Hg, that is required to stop venous blood flow, as detailed, for example, in the mentioned EP 3 068 314 B1.

As the ligature device 1 shown in plan view in FIG. 2A shows, the actuating portion 42 of the rocker 4, which is curved upwards and backwards from the front side with a constant convex curvature, projects into a recess which is symmetrical with respect to the longitudinal direction of the ligature strap 3 fed through and with respect to the longitudinal axis of the closure housing 2, wherein, in the non-actuated rest state of the rocker 4, the top side of the actuating portion 42 and of the top wall 24 of the closure housing 2 merge into one another substantially flush via an intermediate gap of small but perceptible width. Accordingly, the clipping buckle 5 inserted in the rear portion of the closure housing 2 for clipping also merges in its edge region facing the front side substantially flush with the surface via an adapted recess symmetrical to the longitudinal axis in the top side of the top wall 24. This embodiment results in an advantageous operability of the ligature device 1 when the ligature device 1 is fixed to a body part to be ligated in a metered, tension-appropriate manner or respectively when the ligature device 1 is released and/or unclamped.

Usage advantages for operation or handling and storage also result from the attachment of the end piece 6 attached to the front end region of the ligature strap 3. This serves, for example, as a stop to prevent the ligature strap 3 from being unintentionally pulled out of the closure housing 2 and is provided, for example, as shown in FIG. 2A, with a clamping tongue and/or a holding opening as a fastener for storing. The end piece 6 is attached to the ligature strap 3, for example, by means of a clamping receptacle (see FIG. 2B) formed on the rear side of the end piece 6 and/or solely or additionally by means of a material connection such as adhesive bonding or welding.

As FIG. 2B and, in an enlarged section Z, FIG. 2C further show, the ligature strap, as described above, while forming the loop 31 is guided from the rear side into the feed-through shaft 230 formed inside the closure housing 2 between the top side of the rocker plate 41 and the bottom side of an intermediate wall 25 formed in the closure housing 2, and is guided out on the front side through a feed-through opening 43 in the transition region between the front side of the rocker plate 41 and the actuating portion 42 of the rocker 4. The intermediate wall 25 is provided on its bottom side in its front portion located in front of the pivot bearing, which extends to the inner side of the actuating portion 42 except for a small gap for the actuation of the rocker 4, with a holding structure in the form of a front lower edge 241 extending transversely (preferably at right angles) to the longitudinal extension of the closure housing 2, which protrudes towards the top side 32 of the ligature strap 3 and forms a run-up slope towards the rear side and a steep holding flank towards the front side, so that the elastic, rubber-like ligature strap when being pressed against the intermediate wall by pivoting the rocker 4 by pulling downwards on the loop portion 3 inserted at the rear side as a result of the penetrating lower edge 251 by means of the steep front flank is secured against being pulled backwards. The user can loosen the fixation or clamping force of the ligature strap 3 in a metered manner by applying pressure to the actuating portion 42. The intermediate wall 25 with the mentioned holding structure in the form of the front lower edge 251 thus forms an abutment for clamping the ligature strap 3 by means of the rocker 4.

As FIG. 2B and, in particular, 2C further show, in this embodiment the pivot bearing is formed approximately centrally between the front side and the rear side of the closure housing 2 and in the region of the bottom side of the rocker plate 41 is also formed approximately centrally with respect thereto. The elements forming the pivot bearing on the base side of the closure housing 2 and the bottom side of the rocker plate 41 are described in more detail below with reference to FIGS. 3A to 3C and 4A to 4F.

As FIGS. 2B and 2C further show, the rocker plate 41 is provided in its rear lower region with a spring arrangement in the form of a return spring 44, which is preferably integrally formed on the rocker plate 41 in the region behind the pivot bearing and extends obliquely downward to the rear up to near the rear end of the rocker plate 41. The thus tongue-like formed return spring 44 is supported at its rear end region with its bottom side on the top side of the base wall 27 of the closure housing 2, wherein the distance between the bottom side of the return spring 44 and the top side of the rocker plate 41 is dimensioned such that the rocker plate 41 in the unstressed state of the ligature strap 3 (i.e., without downward pull on the strap portion of the loop 31 inserted from the rear side) is aligned at least largely parallel to the bottom side of the intermediate wall 25, so that the ligature strap 3 in any case can be easily displaced in the feed-through shaft 230 without the rocker 4 exerting a clamping force, and thus, for example, the loop width can be varied largely without exerting force prior to a metered fastening to the body part to be ligated taking place. Even after the loop 31 has been opened by unclipping the clipping buckle 5, the ligature strap 3 can thus be easily displaced in the feed-through shaft 230. The ease with which the ligature strap 3 can be displaced in the closure housing 2 also depends to a large extent on the good sliding properties of the ligature strap 3 in the closure housing 2 (which is generally made of a harder plastic). In this case, the feed-through shaft 230 can be designed to be relatively narrow, with only a small amount of play to the cross-sectional contour of the ligature strap 3, so that there is an exact response for clamping when the loop is ligated and for releasing when the loop is loosened.

Furthermore, FIGS. 2B and 2C show the insertion and clipping of the clipping buckle 5 in the closure housing 2 and a fixing of the rear end of the ligature strap 3 in the clipping buckle 5. Accordingly, in the exemplary embodiment shown, the clipping buckle 5 is inserted with a plug-in portion 51 into a receiving shaft 231 formed between the top side of the intermediate wall 25 and the bottom side of the top wall 24 through a rear-side insertion opening 23 on the rear side 22 of the closure housing 2 (see also FIGS. 3A, 3B and 3C) and is clipped therein by means of a latching lug protruding upward from it at its rear region, under abutment with a latching counter lug protruding downwards from the inner side of the top wall 24. In this case, the clipping buckle 5 is brought into abutment with a front edge of a rearwardly protruding actuating part 51 on a rear edge of the top wall 24 of the closure housing 2, optionally, with slight play.

The rear end of the ligature strap 3 is inserted into an insertion slot in the actuating part 50 via a passage open downwardly on the front side thereof and is clamped in the insertion slot and may be additionally fixed therein in a materially bonded manner, for example by adhesive bonding or welding. The ligature strap 3 which is guided out of the passage downward out of the actuating part 50 forms the rear portion of the loop 31, which in the further course transitions into the front portion of the loop and then into the portion guided through the closure housing 2 in the manner described above. By applying relatively light pressure to the top site of the actuating part 50, which is advantageously provided with a slight recess, the clipping buckle 5 can be easily unclipped and pulled out of the closure housing 2 to open the loop 31.

Figures 3A, 3B, 3C:
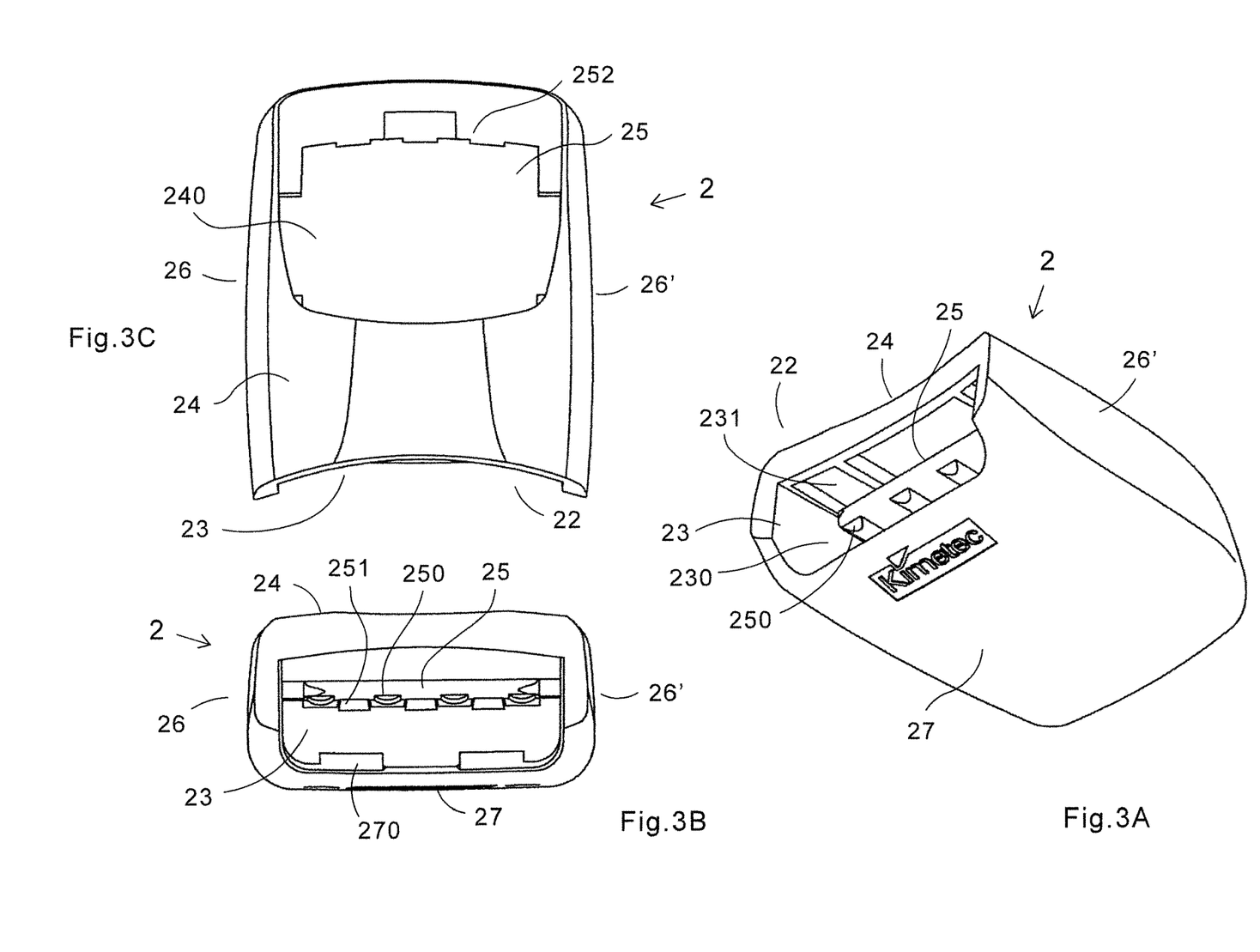
FIG. 3A shows a perspective view of the closure housing from the rear side, obliquely from below.
FIG. 3B shows the closure housing from the rear side.
FIG. 3C shows the closure housing from above.

FIGS. 3A, 3B and 3C show the closure housing 2 in more detail. The closure housing 2, which is preferably made of a non-slip plastic material with good haptics for the operation, is designed in its size to be received in one hand of the operator and to be easily attached to a body part and has smoothly extending curvatures on the outside in its transition areas between the lateral walls to the front side, to the top side and to the bottom site for good handling. The recess 240 in the front region of the top wall 24, into which the actuating portion 42 of the rocker 2 extending in a convex upward direction projects, is shaped according to the contour profile of the upper edge of the actuating portion 42 and is shaped symmetrically with respect to the vertical central longitudinal plane of the closure housing 2, wherein abrupt edges are being avoided by a rounded contour profile. On the rear side 22, the rear edge of the top wall 24 and the adjoining lateral walls 26, 26' is shaped as a slight forward concave indentation symmetrical to the vertical central longitudinal plane of the closure housing 2 and adapted to the contour profile of the front edge of the actuating part 50 of the clipping buckle 5. The concave indentations of the front recess 240 and the rear recess of the top wall 24 result in good guidance for the insertion of the actuating portion 42 and also the clipping buckle 5.

The intermediate wall 25, which in the present case delimits the receiving shaft 231 at the bottom and the feed-through shaft 230 at the top, is provided on its bottom side with integrally formed sliding ribs 250 which extend in the longitudinal direction of the closure housing 2, which are rounded downwards in cross-section (at right angles to the longitudinal axis) and which interact with the top side of the strap 32 of the ligature strap 3 in a friction-reducing manner, so that the latter, in the non-clamped state, can be easily, practically without inhibition, displaced in the feed-through shaft 230 to the desired extent. In the transverse direction between the sliding ribs 250, as can be seen in FIG. 3B, portions of the holding structure in the form of the front lower edge 251 are formed in particular in the front region on the bottom side of the intermediate wall 25, said bottom edge clamping and fixing the ligature strap 3 against the bottom side of the intermediate wall 45 when it is pulled downwards at the portion entering the feed-through shaft from the loop 31 and thus pivoting the rocker 4 upwards with its front portion located in front of the pivot bearing. FIG. 3C also shows the front edge 252 of the intermediate wall 25, at which the sliding ribs and holding structure also extend, in the exemplary embodiment as a toothed front edge 252 in plan view with holding structures (projections, ribs or the like) which are offset in the longitudinal direction and engage in the elastic ligature strap for fixing.

As shown in FIG. 3B in view of the open rear side 22 of the closure housing 2 with the rear insertion opening 23 into the receiving shaft 231 and the feed-through shaft 230, the pivot bearing is formed on the top side of the base wall 27 by means of portions of a rib-like pivot support 270 extending in the transverse direction at right angles to the longitudinal axis of the closure housing 2, on the front side and rear side of which, complementary pivot bearing portions are positioned on the bottom side of the rocker plate 41 when the rocker 4 is inserted. The height of the pivot support 270 up to the bottom side of the rocker plate 41 between the complementary pivot bearing portions is selected in such a way that, in the rest position of the rocker 4, the clear width of the feed-through shaft 230 between the top side of the rocker plate 41 and the bottom side of the intermediate wall 25, in coordination with the thickness of the ligature strap 3, allows the ligature strap 3 to be pulled through practically uninhibited and, and on the other hand, the pivot angle is so large that, by pivoting the rocker 4, the ligature strap 3 is securely clamped against the holding structure between the top side of the front portion of the rocker 4 and the facing bottom side of the intermediate wall 25. Also conceivable is, for example, a pivot bearing of the rocker 4 with bearing parts arranged laterally, for example on the inner side of the two lateral walls 26, 26', into which complementary bearing parts attached to the rocker 4 engage.

Figures 4A, 4B, 4C, 4D, 4E, 4F:
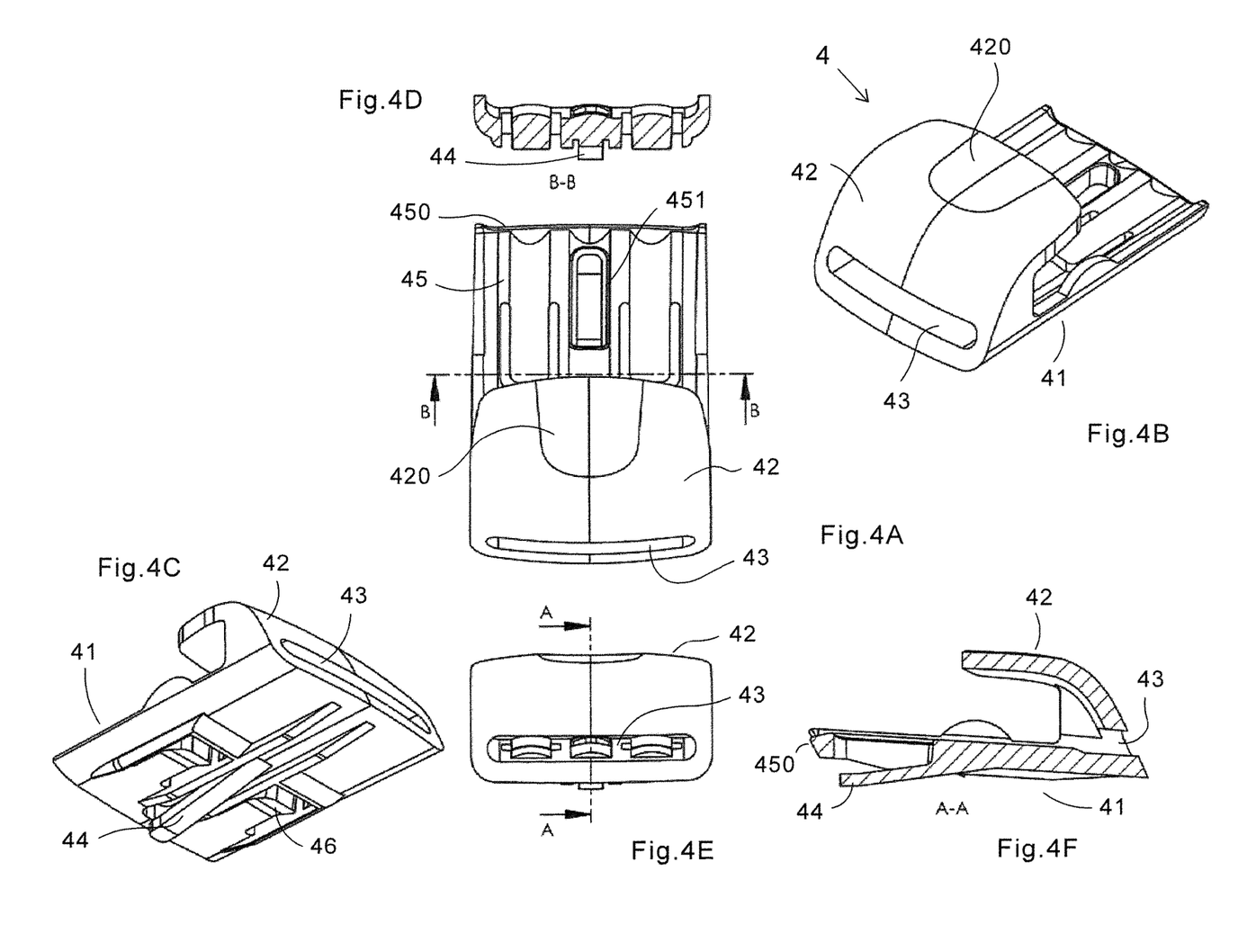
FIG. 4A shows a top view of a rocker insertable into the closure housing for clamping the ligature strap.
FIG. 4B shows the rocker according to FIG. 4A in perspective view obliquely from the front top.
FIG. 4C shows the rocker according to FIG. 4A in perspective view obliquely from the front bottom.
FIG. 4D shows a cross section of the rocker according to FIG. 4A along a section line B-B.
FIG. 4E shows a front view of the rocker according to FIG. 4A.
FIG. 4F shows a longitudinal section of the rocker along a section line A-A according to FIG. 4E.

FIGS. 4A, 4B, 4C, 4D, 4E and 4F show an exemplary embodiment of rocker 4 with more details. Here, in the front region of the rocker plate 41, the actuating section 42 extending under convex curvature upwards and rearwards is integrally formed, wherein in the transition portion located in the front, between the rocker plate 41 and the actuating portion 42, the feed-through opening 43, which is adapted to the cross section of the ligature strap 3 for easy passage, is formed, as shown in particular in FIGS. 4A, 4B, 4C and 4F. As shown in FIG. 4B, a slight actuating recess 420 that is easily palpable by the operator is formed into the top side of the rearwardly extending part of the actuating portion 42. Protruding from the bottom side of the rocker plate 41, in the central region in relation to the transverse direction, behind the relevant elements of the pivot bearing, the return spring 44 protruding obliquely downward toward the rear is arranged in the form of a spring tongue formed on the rocker plate 41. In the transverse direction at right angles to the longitudinal extension, the parts of the pivot bearing interacting with the portions of the pivot support 270 on the top side of the base wall 27 of the closure housing 2 are integrally formed projecting downwards, wherein the partial portions of the pivot support 240 are being received between the front and rear portions of the complementary pivot bearing portions. Here, the rear partial portions are formed on tongue-like portions, which can be resiliently deflected upward in order to insert the rocker 4 into the interior of the closure housing 2 via entry slopes, wherein respective portions at the top side of the rocker plate 41 are being supported against the bottom side of the intermediate wall 25. For inserting the rocker plate 41, the return spring 44 can also be deflected sufficiently far upwards against its pretension. For easy insertion or mounting of the rocker plate 41 in the closure housing 2, guide ribs extending in the longitudinal direction on the bottom side of the rocker plate 41 are also formed with insertion slopes which interact in a guiding manner with corresponding complementary guide structures on the inner side of the base wall 27. The resiliently formed rear complementary pivot bearing portions are shown in FIG. 4C as spring tongues 46.

As shown in FIG. 4A in plan view of the rocker 4, further sliding ribs 45 are advantageously integrally formed on the top side of the rocker plate 41 in order to minimize rubbing of the strap bottom side 33 of the ligature strap 3. The return spring 44 is arranged in a corresponding recess 451 of the rocker plate 41. For insertion and also for easy insertion of the ligature strap 3, the rear edge 450 of the rocker 4 is advantageously beveled or rounded. The rocker 4 is also preferably overall composed of plastic material, so that it facilitates favorable sliding properties for the ligature strap 3 and also secure clamping, and the actuating portion 42 in particular results in good grip and good haptic properties for the actuation by the user.

Advantageously, the closure housing 2, the rocker 4 and/or the ligature strap 3 are designed to be transparent to UV radiation, in particular in the UVC spectral range, so that it is possible to kill harmful germs by means of UV radiation even in regions that are difficult to access mechanically.

The above-described ligature strap 3, which is made of a rubber-elastic material, in particular a silicone strap, smoothed and/or hardened on its outer surface for example by means of a fluoride treatment or by other additives or a treatment with UV radiation, results in combination with the described closure housing 2 and the rocker 4 in substantial advantages of use. However, it can also advantageously be used in another embodiment of the closure housing 2 and the clamping mechanism.

The invention claimed is:

1. A ligature device for body parts, specifically a tourniquet, comprising a closure housing (2) in which a feed-through shaft (230) is formed which extends in the longitudinal direction and is delimited at the bottom by a base wall (27), laterally by two lateral walls (26, 26') and at the top by a top wall (24), and comprising a ligature strap (3) which, by means of a clipping buckle (5) fastened to the one rear end thereof, is clipped or can be clipped detachably to a rear portion of the closure housing (2) and, with the other end thereof, is guided or can be guided from the rear side through the feed-through shaft (230) in order to form a loop (31) of variable size and can be firmly clamped according to the size of a received body part by means of a clamping means, specifically by means of a rocker (4) that is pivotally mounted in a pivot bearing in the closure housing (2), characterized in that
the ligature strap (3) is produced from a rubber-elastic material, such as natural rubber, a thermoplastic elastomer (TPE) or silicone.

2. The ligature device in accordance with claim 1, characterized in that
the ligature strap (3) has a smoothed and/or hardened surface.

3. The ligature device in accordance with claim 2, characterized in that
the surface smoothing and hardening is performed by fluoride treatment of a rubber-elastic strap, specifically a silicone strap, from which the ligature strap is produced.

4. The ligature device according to claim 1, characterized in that
the ligature strap (3) has a rectangular cross-section, wherein the width of the ligature strap (3) is between 10 and 40 mm, preferably between 20 and 30 mm, and the thickness of the ligature strap (3) is between 0.8 and 3 mm, preferably between 1 and 2.5 mm.

5. The ligature device according to claim 1, characterized in that
the top side of the strap (32) and/or the bottom side of the strap (33) is provided with a friction-reducing relief-like structure.

6. The ligature device according to claim 1, characterized in that
the ligature strap (3) is provided with a marking which changes during its elongation and based on which a ligature state of the ligature strap (3) corresponding to a ligature tension can be identified.

7. The ligature device according to claim 1, characterized in that
the ligature strap (3) is transparent, also for radiation in the UV range.

8. The ligature device according to claim 1, characterized in that
the closure housing (2) is transparent to UV radiation, specifically UVC radiation.

9. The ligature device according to claim 1, characterized in that
in the feed-through shaft (230) on at least one side facing the top side of the strap (32) and/or the bottom side of the strap (33), rib-like sliding structures extending in the longitudinal direction of the closure housing (2) protruding from wall portions or from an optionally present rocker (4) are arranged.

10. The ligature device according to claim 1, characterized in that
the rocker (4) is supported on its bottom side in its rear portion located towards the rear side behind the pivot bearing against the top side of the base wall (27) by means of a spring arrangement by means of which the rocker (4) is brought into its non-clamping rest position when the loop (31) is unstressed.

11. The ligature device in accordance with claim 10, characterized in that
the spring arrangement is designed as a return spring (44) formed on the rocker (4) and projecting towards the base wall (27).

12. The ligature device according to claim 1, characterized in that
the ligature strap (3) is provided at its other end, the front end, facing away from the clipping buckle (5), with an end piece (6) designed as a fastener.

* * * * *